US009717785B2

(12) United States Patent
De Almeida et al.

(10) Patent No.: US 9,717,785 B2
(45) Date of Patent: Aug. 1, 2017

(54) RECOMBINANT ANTIGENS OF PORCINE CIRCOVIRUS 2 (PCV-2) FOR V (56) References Cited**

OTHER PUBLICATIONS

Bucarey et al., "The optimized capsid gene of porcine circovirus type 2 expressed in yeast for

RECOMBINANT ANTIGENS OF PORCINE CIRCOVIRUS 2 (PCV-2) FOR VACCINE FORMULATIONS, DIAGNOSTIC KIT AND USE THEREOF

FIELD OF THE INVENTION

The first object of this patent application refers to the capsid purified recombinant protein of the PCV-2 produced in E. coli as vaccine antigens and diagnostic antigen. The second patent object refers to the virus-like particles (VLPs) of the PCV2 produced by E. coli as vaccine antigen or diagnostic antigen. The third object of this application refers to a recombinant vaccine against PCV-2 containing antigens purified or recombinant VLPs of the PCV2 produced in E. coli, added to aluminum hydroxide as adjuvant. The fourth object of patent application refers to a capture ELISA kit for quantifying vaccine antigens of the PCV-2. The vaccine antigens (objects 1 and 2) and the vaccine (Object 3) described herein may be employed for animal's immunization in control programs of PCV-2 associated diseases in conventional swine production systems, and represent alternative to vaccines available in the market. The ELISA kit (Object 4) can be employed for quality testing in commercial and/or experimental vaccines against PCV-2. These products mentioned above may be used in pharmaceutical or animal health field.

STATE OF PRIOR ART

In 1974, porcine circovirus (PCV) was identified for the first time as a persistent contaminant present in a kidney cell culture of porcine origin. However, this virus was associated with a pathogenicity in swine only in the late 90. It was the post-weaning multisystemic wasting syndrome (PMWS), which was first described in Canada. Due to genetic and immunologic differences between this new PCV isolated in the animals with symptoms of PMWS and those contaminants from laboratory cells, these two viruses were named respectively as Porcine circovirus-2 (PCV-2) and Porcine circovirus-1 (PCV -1) (Silva Junior, A., Carvalho, O. V., Bulos, L. H. S., Fietto, J. L. R., Moraes, M. P., Almeida, M. R. Porcine circovirus2: immunopathogenesis and recent developments in vaccines; World journal vaccine, v. 2, p. 96-104, 2012).

Since PCV-2 is associated with a different set of syndromes in swine besides PMWS, the term Porcine circovirus associated disease (PCVAD) was introduced in 2006 by the American Association of Swine Veterinarians (AASV), to group all of these syndromes. In them are included enteritis, reproductive failure, dermatitis, and nephropathy affecting swine, mainly in the phases of growing and finishing. More recently, in 2011, it was described a new syndrome characterized by acute pulmonary edema which affects young animals and vaccinated against PCV-2, leading to a mortality rate of about 200 (Cino-Ozuna A. G., Henry S., Hesse, R., Nietfeld, J. C., Bai, J., Scott, H. M., Rowland, R. R. R. Characterization of a new disease syndrome associated with porcine circovirus type 2 in previously vaccinated herds. Journal of Clinical Microbiology, V.49, p. 2012-2016, 2011). Currently, the PCV-2 has a worldwide distribution and the PCVADs are endemic in most producing countries.

Not all animals infected with PCV-2 present the apparent clinical signs of these diseases. Thus, to perform accurate diagnosis, it is necessary to observe the presence of compatible clinical signs and the presence of characteristic microscopic lesions, besides the detection of the virus in the animal by laboratory techniques such as Polymerase Chain Reaction (PCR), immunohistochemistry (IHC) and among others (Silva Junior, A., Carvalho, O.V., Bulos, L. H. S., Fietto, J. L. R., Moraes, M. P., Almeida, M. R. Porcine circovirus 2: immunopathogenesis and recent developments in vaccines World journal vaccine, v. 2, p. 96-104, 2012).

Since sick animals usually present lymphopenia, secondary infections by opportunistic pathogens are frequent, which increases the importance of PCVAD control. In this sense, studies have been suggested that the development of PCVAD is directly related to virus interaction, as well as other opportunistic infectious agents, with the immune system of the animal demonstrating the multifactorial nature of these diseases (Silva Junior, A., Carvalho, O. V., Bulos, L. H. S., Fietto, J. L. R., Moraes, M. P., Almeida, M. R. Porcine circovirus 2: immunopathogenesis and recent developments in vaccines World journal vaccine, v. 2, p. 96-104, 2012).

0 PCV-2 can be spread in the environment through oral and nasal secretions, feces and blood. The virus transmission occurs by nasal, oral, fecal path and the urinary tract. The infectious viral particle is resistant to physical and chemical factors, and is able to withstand acidic environments (pH 3), heat inactivation (120° C. for 30 minutes), freezing, and exposure to ultraviolet light. Potassium monopersulfate based disinfectants, peracetic acid with hydrogen peroxide, compounds containing quaternary ammonium salts, sodium hypochlorite, or sodium hydroxide are effective in reducing the number of infectious particles. On the other hand, products containing iodine or phenolic compounds are not able to reduce the infectivity of the virus in vitro. Because of the multifactorial nature of PCVAD, its control should be done through a combination of factors such as good management practices recommended by the well-known "Madec's 20 points", the reduction of animal stress, reduction in mixing batches, the adoption of health gaps, as well as vaccination and serological surveillance of the herd, has proven efficients (Madec, F., Rose, N., Grasland, B., Cariolet, R., Jestin, A. Post-weaning multisystemic wasting syndrome and other PCV2-related problems in pigs: a 12-year experience. Transboundary and Emerging Diseases, V. 55, p. 273-283, 2008).

Since the emergence of PMWS and the confirmation of the PCV-2 and its causal agent, researchers around the world have been devoted to developing ways to control this disease, especially through vaccines. Several strategies have been employed in order to develop immunogens. Among them, inactivated virus vaccines grown in cell culture, the DNA vaccines, and the subunit vaccines containing the protein of the viral capsid produced in modified insect cells stand out (Silva Junior, A., Carvalho, O. V., Bulos, L. H. S., Fietto, J. L. R., Moraes, M. P., Almeida, M. R. Porcine circovirus 2: immunopathogenesis and recent developments in vaccines World journal vaccine, v. 2, p. 96-104, 2012).

The structural protein of the circovirus capsid, SEQ ID NO: 04, is encoded by ORF2, SEQ ID NO: 03, and has an approximate molecular mass of 28 kDa and theoretical isoelectric point (PI) of about 10.7. By interacting specifically with receptors on the cell surface, it is the most relevant protein involved in the host immune response. It has a nuclear localization signal at its amino terminal portion (first 41 amino acid residues) with a large number of positively charged amino acid residues, where about 40% are arginine residues. Studies showed that the presence of three immunogenic epitopes on the capsid protein of the PCV-2 are capable of generating neutralizing antibodies. These comprise the amino acid sequences 47 to 57, from 165 to 200 and the last four amino acid residues from the C-terminus (Lekcharoensuk, P., Morozov, I., Marsh, P. S., Thangthumniyom, N., Wajjawalku, W., Meng, X. J. Epitope mapping of the major capsid protein of type 2 porcine circovirus (PCV2) by using chimeric PCV1 and PCV2. Journal of Virology, V. 78, p. 8135-8145, 2004).

The viral capsid protein of the PCV-2 was first produced in *Escherichia coli* in 2001 by Liu and co-workers as a polypeptide chain fused to the maltose binding protein (MBP) and a histidine tail—(MBP)-His8 (Liu, Q., Tikoo, S. K., Babiuk, L. A. Nuclear localization of the ORF2 protein encoded by porcine circovirus type 2. Virology, v. 285, p. 91-99, 2001). This recombinant protein purified by affinity chromatography reacted specifically with both the rabbit polyclonal sera previously immunized with PCV-2 and the sera from swine infected by the virus.

There is a difficulty in expressing large quantities of capsid protein of the PCV-2 in *Escherichia coli* cells due to the large amount of arginine residue in the nuclear localization signal and the presence of other amino acid residues synthesized from rare codons for this organism. Another way to circumvent the problem of low expression of the capsid protein of the PCV-2 is using bacterial strains that overexpress t-RNAs of rare codons, such as BL21 codon-plus-DE3-RIL. The advantage is the maintenance of all amino acid residues of the protein (primary structure is conserved), which ensures the possibility of antibodies generation produced from the epitopes present in the nuclear localization signal region. However, other bacterial systems marketed or developed by companies can be used for expression.

Currently, the recombinant Cap-PCV-2 expression is done, mainly, in two systems: the first uses of insect cells infected with recombinant baculovirus, while the other consists of the induction of recombinant protein in transformed bacterial systems. In the latter, the expression system is usually subject to the control of the lac operator, so that its induction is commonly done by adding Isopropyl-β-D-1-thiogalactopyranoside (IPTG) to the growth medium. However, there are several vectors for expression in bacterial systems marketed by various companies. Thus, other promoters, homologous or heterologous, may also be used as promoters subject to modulation by arabinose. Virus-like particles (VLPs) are structural proteins of the viral capsid, which are arranged in a structure similar to the wild viral particle forming a capsid lacking the genetic material therein. These non-infectious particles have high immunogenicity due to present the structural form of virions (viral infectious particle). Therefore, the use of VLPs in the recombinant vaccines increase the efficiency of such vaccines by stimulating the immune system in a manner similar to the wild viral particle. It has been demonstrated the forming ability of VLPs by the capside protein of the PCV-2 in both eukaryotic expression systems (Bucarey S. A., Noriega, J., Reyes, P., Tapia, C., Saenz, L. Zuniga, A. Tobar, J. A. The optimized capsid gene of porcine circovirus type 2 expressed in yeast forms virus-like particles and elicits antibody responses in mice fed with recombinant yeast extracts. Vaccine, v. 27, p. 5781-5790, 2009), and in prokaryotic systems (Lou, Z. Z., Li, Z. Y., Wang, G., Li, J. Q., Lan, X., Li, X. R., Yin, X. P., Liu, J. X., Liu S. D. Prokaryotic expression and potential application of the truncated PCV-2 capsid protein. Virological Sinica, v. 25, p. 86-97, 2010).

The methodology used in the present invention uses bacterial system. This is capable of generating amounts of antigen in the range of tens to hundreds of milligrams per liter of medium induced within a few hours of induction. However, the expression system in insect cells requires days to produce the same. Another advantage is the costs associated with its production. The bacterial system uses cheaper induction means than that of insect cells. Yet, systems employing insect cells do not require subsequent steps from the expression for the concentration and purification of the antigen. However, in the present invention, the recombinant antigens are recovered by means of less expensive techniques for later use.

Another possible disadvantage of bacterial system is the lack of post-translational modifications in the capsid protein, once it is a prokaryotic system. However, the present invention shows that the viral capsid protein, when expressed in a bacterial system, is able to self-assemble and to promote generation of non-infectious VLPs with similar shape and size to the wild viral particles, similar to that observed for expression in eukaryotic systems.

Another difficulty encountered in the production of a vaccinal compound containing the viral capsid protein of the PCV-2 is its quantification in vaccinal formulation. The recombinant vaccines on the market usually use the quantification technology by densitometry in polyacrylamide gel, using as reference a standard protein such as bovine serum albumin (BSA). In this application, use is made of anti-PCV-2 antibodies for quantifying the immunogenic protein. Such antibodies specifically interact with the capsid protein of the PCV-2 present in a particular sample, and due to specific marker on the antibody a signal generation occurs (color, radioactivity, etc.) proportional to the amount of antigen present in the sample. Thus, the quantification occurs upon the reading of this produced signal and by means of a comparison with a sample containing the purified recombinant protein.

Several enhancers of immune responses are described in the literature and, according to the present invention, may be used in conjunction with the formulations described herein. Aqueous adjuvants such as aluminum hydroxide or carbon polymers, such as carboxymethyl cellulose, are preferred due to generation of less inflammation and pain than oily adjuvants.

The vaccinal compounds developed in the present invention may be administered in any of the routes described in the literature, preferably, intramuscularly.

In the search done in patent banks, patent documents in the immunogens production processes area for swine were found, however none of these patents uses products or processes related to the object of this patent. In this search, the patent document PI 0412855-9 of Jul. 26, 2004, entitled VACCINE FORMULATIONS, which refers to "a new oil-water emulsion with increased stability in the presence of bacterial or viral suspensions, especially those concentrated and non-purified or weakly purified" was found, wherein it is described a solution containing the inactivated PCV-2. The object of the present patent application is different from the described patent because it focuses on the use of the recombinant protein produced in bacterial system, in addition to propose specific new procedures for recovery and quantification of this antigen.

Another application found was the one of number BRPI0615862-5 of Sep. 8, 2006, entitled VACCINE PCV-2, AND, METHOD FOR MANUFACTURING A VACCINE, which is "a vaccine against porcine circovirus (PCV-2) and a method for manufacturing such a vaccine to protect swine against infection with PCV," in which the inventors have developed a process for the production of recombinant antigens, preferably in eukaryotic system (insect cells) in order to circumvent the problem of virus particles low recovering in cultured cells. Similar to this patent, on Dec. 29, 2005, U.S. Pat. No. 770.028 was filed in the US patent database, which has the title: "PCV2 immunogenic compositions and methods of producing such compositions," which describes a method for improved recovery of capsid recombinant protein of the PCV-2 in the supernatant of the induced cells, beginning about 5 days after infection. In contrast, the present invention provides the production of tens to hundreds of milligrams of proteins in a few hours of induction, after lysis and recovery of the recombinant protein.

Figure 10:
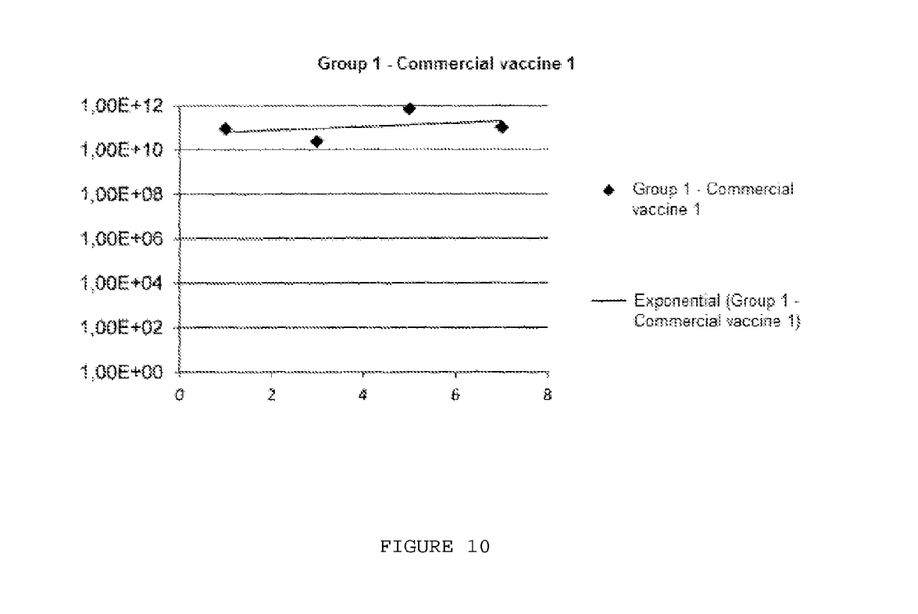

Another deposit found in US patent database is the U.S. Pat. No. 8,008,001, of Dec. 11, 2009, entitled "PCV-2 VACCINE" which deals with a vaccine and a method to protect piglets against PCV-2 infection by administering a vaccine containing at least 20 microgram/dose of capsid protein of the PCV-2. Such patent discloses the preferred use of eukaryotic expression system (insect cells inoculated with recombinant baculovirus). This system differs from that proposed in the present invention, as described herein is the use of bacterial systems, with new methods for the antigen recovery and quantification.

It was also found in the US patent database, the patent U.S. Pat. No. 6,287,856 of Mar. 12, 1999, entitled "Vaccines against circovirus infections", which deals with vaccine compositions that are protective against PCV infections. They are based on nucleic acid vector containing the coding sequence for a PCV polypeptide, where the nucleic acid is lacking a viral replication origin, thus regarding to DNA vaccines, other than the present application, which produces the antigen in E. coli.

The first object of this patent application is the purified recombinant capsid protein of the PCV-2 produced in genetically modified *E. coli* as vaccinal antigen and diagnostic antigen. The second patent object is the virus-like particles (VLPs) of PCV2 produced by genetically modified *E. coli* as vaccine antigen. Both objects can be used in control and prevention programs of infection caused by PCV-2. The third object of this application is a recombinant vaccine against PCV-2 containing PCV2 purified antigen or recombinant VLPs, or its variants produced in genetically modified *E. coli* with the addition of aluminum hydroxide as adjuvant. As well to be used in control and prevention programs of infection caused by PCV-2.

It is also object of the present invention to provide a capture ELISA Kit by means of recombinant protein produced for further quantification in vaccine formulations. This technique has as main advantages its ease of execution and automation, precision, adaptability and low cost. Moreover, the main advantage of the proposed capture ELISA is that the samples do not need to be purified nor high concentrations to be assayed, since the antigen is fixed by specific antibodies making this connection proportional to the concentration of these proteins, resulting in greater reproducibility in the results where the quantification is required. Very low amounts, such as 50 micrograms of protein can be detected when diluted with one liter of solution. Thus, due to its benefits and facilities, this essay presents itself as a strong candidate to be used as a reference in safety testing and dose-response assays to verify the vaccinal power required for the release of different commercial vaccines, adapted as necessary.

The development of immunogenic compounds able to generate protection against the infection of the PCV-2 has been a targeted search within the general framework of research control of PCVAD. The capsid recombinant protein of the PCV-2, produced in bacterial system and recovered in the way described above, points as a potential immunogen. Additionally, the replacement of laborious techniques for the detection and quantification of the PCV-2 as a diagnostic method is something of interest for veterinary diagnostics industry. Thus, the investment in production and recovery of the recombinant antigens disclosed herein for producing target compounds for diagnostic and vaccine purposes as well as for other applications is very promising.

DESCRIPTION OF THE DRAWINGS

FIG. 01 shows the analysis in 1% agarose gel of PCR products. M: Ladder DNA marker 100 bp; 1, 2, 3, and 4: DNA corresponding to ORF2 of amplified PCV-2; C-: negative control (DNA extracted from SK6 cells free of PCV-2).

FIG. 02 shows the analysis in 1% agarose gel of the cleavage reactions of the plasmids with EcoRI, showing the bands of 400 and 316 bp from the cleavage of ORF2. M: Ladder DNA marker 100 bp; 1.1, 1.2, 1.4, 1.6, and 1.8: white colonies chosen at random; 1.9, 1.10 and 1.11: negative control (blue colonies).

FIG. 03 shows the analysis in 1% agarose gel of cleavage reactions of the pCap-PCV2 recombinant plasmid with EcoRI (channel 1) and with XbaI (channel 2). M: Ladder DNA marker 100 bp.

FIG. 04 shows the confirmation of rCap-PCV-2 expression. 15% SDS-PAGE gel (left) and nitrocellulose membrane obtained by Western blotting (right). M: molecular weight marker; C−: negative control (soluble fraction of *E. coli* extract transformed with the plasmid of empty bacterial expression and induced with IPTG); and 2: Sample (soluble fraction of *E. coli* extract transformed with the pCap-rPCV2 and induced with IPTG). The arrow indicates the band of approximately 30 kDa corresponding to rCap-PCV-2.

FIG. 05 shows the protein profile obtained during the purification process from the soluble fraction. M: molecular weight marker; 1: soluble fraction of induced *E. coli* extract; 2: non-interacting volume; 3: wash with 10% elution buffer; 4: Wash with 20% elution buffer; 5: elution with 100% elution buffer. The arrow indicates the purified rCap-PCV-2.

FIG. 06 shows the protein profile of the resulting fractions from the process of precipitation of the soluble fraction with different levels of saturation with ammonium sulfate. M: molecular weight marker; 1: soluble fraction, 2: Fraction 0-20%, 3: Fraction 20-40%, 4: Fraction 40-60%, 5: Fraction 60-80%, 6: Purified rCap. The arrow indicates the rCap-PCV-2.

FIG. 07 A, B, and C show electron micrographs: formation of virus-like particles (VLPs) by rCap-PCV-2. Increased 140000X (A and B). Increased 250000X (C). The samples were analyzed by Transmission Electron Microscope, with 200 mesh grids covered with formvar/carbon being used. VLPs can be visualized by the arrows.

FIG. 08 shows sample dilutions: rCap-PCV-2: 10 mg/L to 0.004883 mg/L dilutions. Vaccinal candidate: 1:50 to 1:103, 200 dilution. Lysate from Negative E. coli: 1:50 to 1:103, 200 dilutions. The obtained equation is $y=0.875x+0.196$ ($R^2=0{,}996$), where y is the OD 492 nm and x is the concentration of the protein to be detected.

FIG. 09 shows the specific humoral response induced by rCap-PCV-2 in mice before and after vaccination as measured by indirect ELISA. The animals were inoculated on days 0 and 14 and challenged on day 35. The inoculated animals with the vaccinal candidate showed significant amounts of antibodies, especially after the second inoculation.

FIG. 10 shows assessment of viremia of vaccinated animals with the commercial vaccine 1 at sampling time. On the vertical axis is shown the viral load, on the horizontal axis is shown the 4 collection steps: 21, 63, 105 and 154 days of swine age. The linear regression is represented by the formula y=5E+10$e^{0.1847x}$. There was no significant reduction in viral load during the period after the vaccination ($R^2$=0.1195).

FIG. 11 shows the viremia assessment of the animals vaccinated with the commercial vaccine at two sampling times. On the vertical axis is shown the viral load, on the horizontal axis is shown the 4 collection steps: 21, 63, 105 and 154 days of swine age. The linear regression is represented by the formula y=2E+13$e^{-1.323x}$. There was no significant reduction in viral load during period after the vaccination ($R^2$=0.5703).

FIG. 16 shows viremia assessment at the collecting times of the unvaccinated animals (negative control). On the vertical axis is shown the viral load, on the horizontal axis is shown the 4 collection steps: 21, 63, 105 and 154 days of swine age. The linear regression is represented by the formula y=2E+13$e^{-1.304x}$. There was no significant reduction in viral load on the period after the vaccination ($R^2$=0.7425).

DETAILED DESCRIPTION OF THE INVENTION

Figure 1:
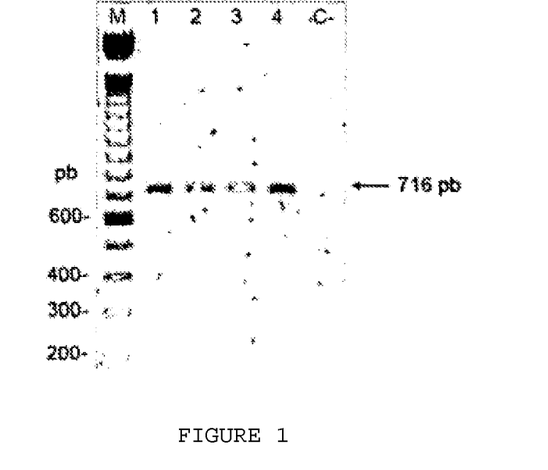

Isolation and Cloning of the Coding Region of the Porcine circovirus Capsid Protein The DNA the *Porcine circovirus* 2 (PCV-2) used in the amplification of the coding region of the capsid protein (ORF2), SEQ ID NO: 03, was isolated from swine tissue samples afflicted with PCV-2, from Ponte Nova region, MG. The ORF2 was amplified by the technique of Polymerase Chain Reaction (PCR) using the direct oligonucleotide 5'-CGCCATATGACGTATCCAAGGAGG-3' (Forward), which inserts a restriction site for the NdeI enzyme at 5' end and the reverse oligonucleotide 5'-CCCTC-GAGTTAGGGTTTAAGTGGG-3' (Reverse), which creates a site for XhoI at the end of the coding region. These oligonucleotides were constructed from the genome sequence of the Brazilian isolated of PCV-2 (DQ364650) deposited in the GenBank. The amplification of DNA fragments was performed in a thermocycler using Taq DNA Polymerase 5 U/µL. The amplified samples were stored at −4° C. and analyzed by horizontal electrophoresis on a 1% agarose gel. The DNA fragment of 716 bp was evidenced on the gel with ethidium bromide 0.4 g/mL, under ultraviolet light, as shown in the FIG. 01.

The PCR product was purified from agarose gel. Then the purified PCV-2 ORF2 was cloned into an amplification vector (pGEM®-T Easy Vector System PROMEGA). The binding mixture obtained as indicated by the kit manufacturer was added to approximately 100 µL of solution containing bacteria *E. coli* DH5α, rendered competent beforehand (Sambrook J., Russell, D. W., Molecular Cloning: A laboratory manual. 3rd ed, Cold Spring Harbor Laboratory Press, New York, 2001), and incubation carried out for 30 min in ice. Then, the mixture of cells and plasmid DNA was subjected to a thermal shock in a water bath at 42° C. for 1 minute, and again on ice for 2 minutes. Subsequently, 900 µL of LB-Net (1% tryptone, 0.5% yeast extract, 1% NaCl; pH 7.5) without antibiotic was added and cells incubated at 37° C. for 2 hours at 250 rpm in orbital shaker. This mixture was plated on solid LB-agar medium (1% tryptone, 0.5% yeast extract, 1% NaCl, 1.5% Select agar; pH 7.5) containing ampicillin (5 to 10 mg/mL) and incubated for 12 to 14 h at 37° C.

Figure 2:
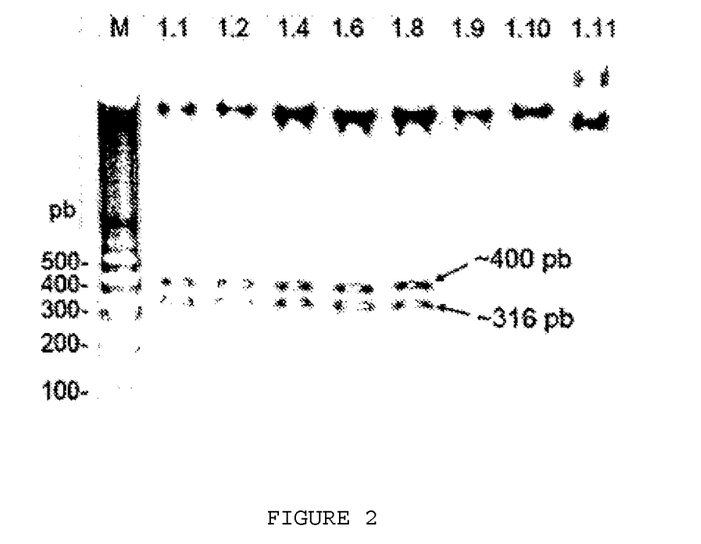

The ampicillin-resistant clones were recovered and used to confirm the presence of plasmid containing the gene of interest by means of PCR and enzymatic assay from the plasmid extracted by mini plasmid preparations (Sambrook J., Russell, D. W., Molecular Cloning: A laboratory manual. 3rd ed., Cold Spring Harbor Laboratory Press, New York, 2001). The enzymatic assay was performed with the restriction enzyme EcoRI and subsequent cleavage reaction analyzed by electrophoresis in 1% agarose gel (FIG. 02). The PCR of colony was performed in the same way that the PCR described above, however, in place of genomic DNA from infected tissues was added an aliquot of the transformant colonies with the aid of sterile sticks. The PCR products were also analyzed by electrophoresis on 1% agarose gel.

The plasmid samples obtained containing the viral DNA, confirmed by enzyme assay and PCR of colony, were purified using a PCR product purification kit and then sent to the Genomics Laboratory, BIOAGRO/UFV for subsequent sequencing to confirm the correct assembly of vector. The sequencing reactions were based on chain termination technique by dideoxynucleotides (ddNTPs) (Sanger, F., Nicklen, S., Coulson, A. R. DNA sequencing with chain-terminating inhibitors. Proceedings of the National Academy of Sciences, V. 74, p. 5463-5467, 1977). The generated sequences were edited and assembled in "contigs" using bioinformatics software and, subsequently, compared with each other and have the sequences deposited in the GenBank using the BLAST software. The translated sequence of ORF2 is described in SEQ ID NO: 04. The clones containing the construct were stored in LB-Net medium in microcentrifuge tubes with 20% glycerol and stored at −80° C.

Figure 3:
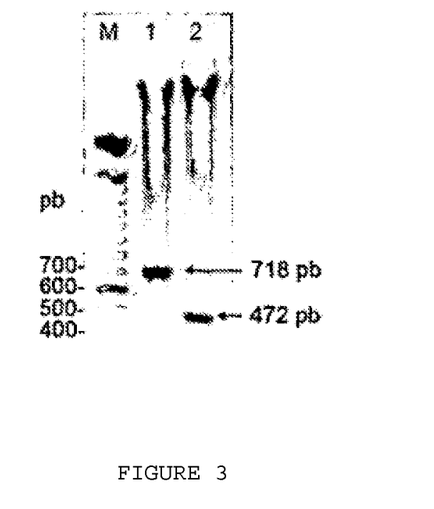

Transfer of the Coding Region of the Porcine circovirus2 Capsid Protein to the Expression Vector in Bacterial System After checking the correct sequence of the insert in the vector, the pCapPCV-2 plasmid DNA sample, SEQ ID NO: 03, (amplification vector) was subjected to an enzymatic assay where specific restriction sites were used to insert the ORF2 gene into a bacterial expression vector (pET-16b -Novagen), which is controlled by the lac T7 promoter and has a sequence that encodes for a 10 histidine tail at the N-terminal (used for purification through affinity with nickel containing resin). The sequence of the ORF2 in the pCapPCV-2 was digested with NdeI and XhoI, as well as the bacterial expression vector. After cleavage, the products (digested bacterial expression vector and ORF2 insert removed from the amplification vector) were bound using T4 DNA ligase enzyme. The bind reaction was then used to transform E. coli DH5α; as described above. The transformant clones were randomly selected from the colonies to identify plasmids with the insert. For the cloning confirmation colony PCRs were performed showing that the site directed cloning work as expected for the two groups of randomly chosen colonies, giving rise to a fragment of 716 bp. Positive colonies were selected and each colony was subjected to PCR separately. For the colony that presented the recombinant plasmid with the approximate size of 716 bp, cleavage reactions of the PCAP-RPCV-2 plasmid were carried out, SEQ ID NO: 01, to confirm their correct orientation. Thus, the expected size bands of 718 by and 472 bp were observed from the digestion with EcoRI and XbaI, respectively, and a high molecular weight corresponding to the remaining fragment of the plasmid (FIG. 03). The recombinant plasmids obtained were named PCAP-rPCV2 and stored in microcentrifuge tubes containing 15 to 30% glycerol, and stored at −70° C.

Expression of the Recombinant Protein of the Porcine circovirus 2 Capsid and Analysis on SDS-PAGE Gel The full expression of the recombinant proteins was performed in medium scale in TB 1000 mL (tryptone 12 g/L, yeast extract 24 g/L, glycerol 4 mL, monobasic potassium phosphate 2.31 g/L, and dibasic potassium phosphate 12.54 g/L). For this, competent bacteria, of the strain E. coli BL21-DE3-RIL codon plus, were transformed with the PCAP-rPCV2 constructs, analogously to that carried out with the amplification vector. Thus, approximately 20 nanograms of PCAP-rPCV2 recombinant plasmid were added to 100 L of competent cells and the mixture incubated on ice for 30 min. Then, the cells mixture and plasmid DNA were subjected to a thermal shock in a water bath at 42° C. for 1 minute, and again on ice for 2 minutes. Thereafter, 900 μL of LB medium (bacto-tryptone 10 g/L, yeast extract 5 g/L, and sodium chloride 10 g/L) without antibiotic was added and the cells incubated at 37° C. for 2 hours 250 rpm. The cells were hundred-fold diluted (1:100) into LB medium containing ampicillin 50 μg/mL and incubated at 37° C. and 200 rpm for 12 hours (pre-inoculation). A culture of the negative control (non-transformed BL21 bacteria) was also performed in LB-Net, pH 7.0, chloramphenicol 17 μg/mL. The cells were then diluted 1:100 in TB liquid medium, pH 7.0, with ampicillin 100 μg/mL and the culture was grown at 30° C./250 rpm for approximately 3 hours until the optical density ($OD_{600}$) of 0.6-0.8 was reached. The same procedure was done for the negative control using chloramphenicol 17 μg/mL. After reached the OD, the culture aliquots were transferred to new tubes where inductions were made for 1, 2, 3, 4, and 5 hours to know the best induction time. The IPTG concentrations tested were 0.1; 0.5 and 1 mM and the temperatures used were 30° C. and 37° C., always under vigorous agitation and sufficient aeration. With the negative control, the same procedure was carried out. 1 mL samples at each condition were collected, centrifuged at 10000×g for 1 min, the supernatant discarded, and the cell pellet stored at −20° C. for analysis by SDS-PAGE.

For purification, the best production time (4 hours), temperature (30° C.), and concentrations of IPTG (0.25 mM) were observed during the induction and, therefore, 1 liter of growing colonies containing the recombinant plasmid pCap-rPCV2 was induced. After induction at the optimal conditions, the sample was centrifuged at 10,000 g for 20 min at 4° C. The supernatant was discarded and the cell pellet was stored at −20° C.

The precipitate resulting from a volume of 100 mL of the induced medium was thawed and resuspended with lysis buffer ($NaH_2PO_4$ 20 mM; NaCl 300 mM, Imidazol 5 mM, pH 8.0) to a final volume of approximately 2.5 mL. To this buffer, lysozyme at 1 mg/mL was added and then the sample was incubated at 0° C. for 30 min. The cell lysis process was performed with 6 sonication cycles of 10 s at 200-300 watts each, with intervals of 10 s and with the tubes on ice to prevent sample warming. Cellular debris and the inclusion bodies were precipitated by centrifugation at 15000×g for min at 4° C. The supernatant (soluble fraction) was collected in a new tube and used for the purification of capsid recombinant protein of the PCV-2, named rCap-PCV-2 (SEQ ID NO: 02).

Figure 4:
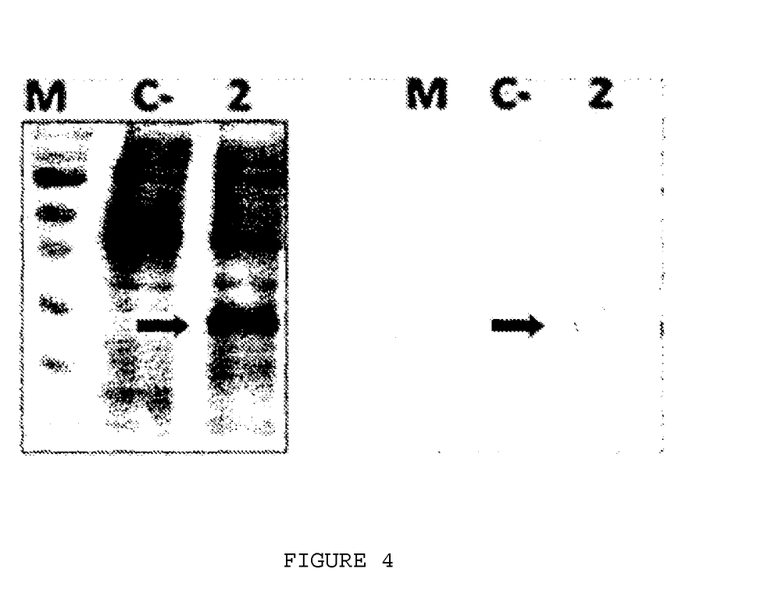

The samples (including negative controls) were analyzed in 15% polyacrylamide gel (Sambrook J., Russell D. W., Molecular Cloning: A laboratory manual. 3rd ed, Cold Spring Harbor Laboratory Press, New York, 2001). After the run, the gel was revealed by staining solution (Coomassie Brilliant Blue R-250 0.1%, acetic acid 9%, ethanol 45%). The electrophoresis running confirmed the presence of a band of approximately 30 kDa present in the induced sample. This mass corresponds to the protein encoded by ORF2 of the PCV-2 added to the histidine tail. The expression confirmation was carried out through the Western blotting technique (FIG. 04).

Figure 5:
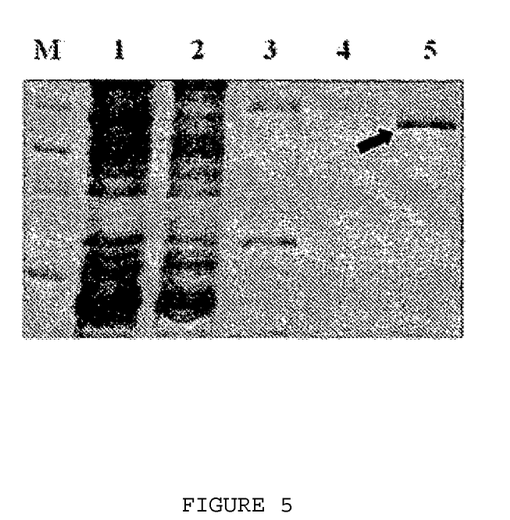

Purification of Capsid Recombinant Protein of Porcine circovirus 2 and Analysis on SDS-PAGE Gel The viral capsid recombinant protein of the PCV-2 was purified from the soluble fraction by means of affinity chromatography in agarose immobilized nickel resin. The technique used was the "Fast performance liquid chromatography" (FPLC), with chromatographic column charged with nickel for purification of the recombinant proteins fused to histidine tails. The purification was standardized by means of several analysis parameters as: linear flow, wash and elution volumes, and imidazole and urea concentrations. After purification, the solution containing the protein was dialyzed three times in 50 volumes of carbonate buffer 50 mM pH 7.2 containing NaCl 300 mM in a total of nine hours (three-hour dialysis). Samples of all purification steps were analyzed on polyacrylamide gel 15% as previously described. The protein was successfully purified and can be seen in FIG. 05.

rCap-PCV-2 Concentration Estimation

The quantity of purified and dialyzed recombinant protein of viral capsid of the PCV-2 may be determined using the method described by Bradford (Bradford, M. M., 1976, A rapid and sensitive method for the quantitation of microgram quantities of protein utilizing the Principle of protein—dyebinding. Analytical Biochemistry, V. 72, p. 248-254, 1976). The calculation is made by linear regression where the equation $y=0.3267+0.0108x$ was obtained from the best fit to the optical density values for the BSA dilutions tested. Recovery of Recombinant Protein of Porcine circovirus 2 Capsid by Precipitation with Ammonium Sulfate and Preparation of the Vaccinal Compound and Formation Verification of the Virus-Like Particles (VLPs)

Figure 6:
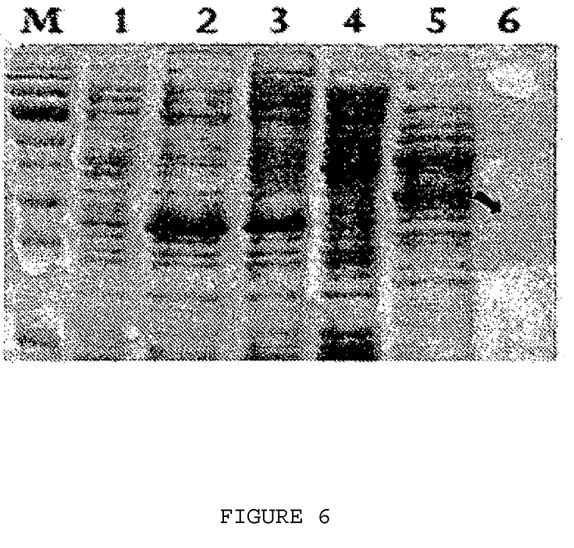

For this, to the soluble fraction containing the rCap-PCV-2, was added an amount of $Na_2SO_4$ sufficient for 20% saturation (to 0°) and, subsequently, the sample was incubated on ice, 100 rpm for 30 minutes. Next, the protein extract was centrifuged at 15,000×g for 20 minutes at 0° C. At the end of centrifugation, the supernatant was collected and the precipitate resuspended in the same carbonate buffer volume pH 7.0 containing NaCl 300 mM (protein fraction of ammonium sulfate 0-20%). To the supernatant, an amount of $Na_2SO_4$ sufficient to saturation 40% was added, starting from an initial 20% saturation of this salt solution. Then, the incubation and stirring on ice and centrifugation steps were repeated to obtain fractions of ammonium sulfate with saturation 20-40%, 40-60%, and 60-80%. The fractions were dialyzed in carbonate buffer pH 7.0 containing NaCl 300 mM and then stored at 4° C. for, at most, two days to be analyzed by SDS-PAGE (FIG. 06), Western blotting, and Capture ELISA. Was used per vaccine 1 mL dose of the adjuvant aluminum hydroxide gel (OMEGA—Chemicals Inc.).

Figure 7:
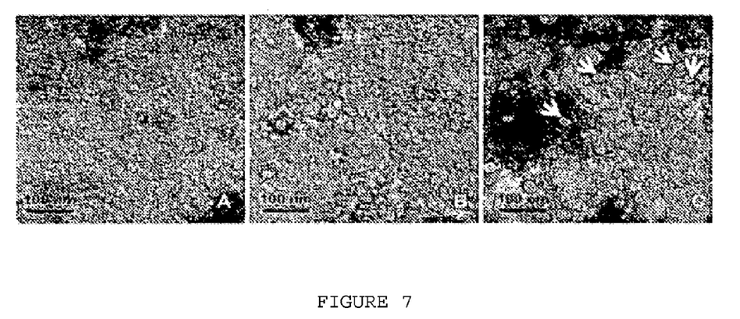

For VLPs verification, fractions from the CsCl gradient with a positive result on the Western-blotting were dialyzed separately against 500 mL of carbonate buffer (NaCl 300 mM, carbonate 50 mM, pH 7.0), 2 times each for 4 hours. Approximately, 10 μL of each fraction were added to the formvar/carbon covered 200 mesh grids and allowed to stand for 1 minute at room temperature. Then, the excess sample was removed with filter paper and a drop of uranyl acetate 2% was added in each grid and allowed to act for 1 minute. The excess of this contrast was removed with filter paper and the grids were left in a desiccator for 2 days. The analysis was performed on a transmission electron microscope and the images were photographed (FIGS. 07 A, B and C).

Quantification of PCV2 Vaccine Antigens by Capture ELISA

Figure 8:
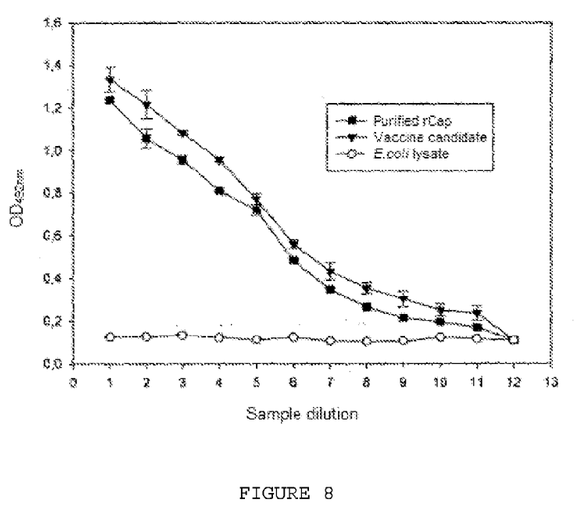

In this ELISA assay, anti-rcap-PCV-2 antibodies raised in rabbit were precipitated and used as capture and detection antibodies, the latter being conjugated with peroxidase. In the standardization, the optimal antigen concentration was 0.625 g/mL, the optimal dilution of the catching antibody was of 15 μg/mL, and the peroxidase conjugate detection antibody was of 1:800. All procedures were performed according to Checkerboard method (Crowther J. R. ELISA. Theory and Practice. Methods in Molecular Biology. V. 42, p. 1-223, 1995). After optimization of the capture ELISA working conditions, concentrations of rCap-PCV-2 were used to construct a standard curve (y=0.196+0,875x) by linear regression (FIG. 08). The construction of the standard curve was performed by calculating the mean of the absorbance values obtained from serial dilution, at base 2, of the protein, starting from 5 mg/L to 0.0048 mg/L, in a 96 wells microplate coated with the capture antibody at 0.625 g/mL of concentration. The working range of the assay was defined as the linear region of the curve with a correlation coefficient of $R^2$=0.996. Thus, the seven-point calibration were from rCap-PCV-2 0.625 to 0.0391 mg/L corresponding to the result of linear regression analysis.

For the quantification of the protein in vaccinal compound 0.6 g of the precipitate were used, equivalent to 100 mL of cells induced medium of transformed *E. coli* with the pCap-2-RPCV recombinant plasmid containing the gene corresponding to the ORF2 of the PCV-2 and induced with IPTG for the recombinant protein production. As a negative sample, the same amount of extract of transformed cells was used with the empty bacterial expression vector. The precipitates of these cells were thawed and resuspended in lysis buffer 2 mL ($NaH_2PO_4$ 20 mM, NaCl 300 mM, Imidazole 5 mM, pH 8.0). To the lysis buffer lysozyme 1 mg/mL, 1 mM PMSF were added and then incubated on ice for 30 minutes. The process of cell lysis was performed with 6 sonication cycles of 10 seconds at 200-300 W each, with 10 seconds intervals and the with tubes on ice to prevent warming of samples. The unknown concentration of rCap-PCV-2 in vaccinal candidate was determined by Holden and colleagues (Holden, L., Faeste, C. K., Egaas, E. Quantitative Sandwich ELISA for the determination of lupine-lupinus spp. in foods. Journal of Agriculture Food Chemistry, V. 53, p. 5866-5871, 2005), where vaccine serial dilutions were performed and the dilution at which the OD 492 nm value closest to the midpoint of the linear portion of the standard curve was used to calculate the concentration of the protein in the vaccine. Thus, the concentration of rCap-PCV-2 (SEQ ID NO: 02) in the vaccinal candidate, after the calculation of the sample dilution factor, was 0.73 mg/mL.

Demonstrative Experiments

Experiments in Mice

Female mice of five weeks old were divided into four groups of five animals each as follows: one group for the developed vaccinal candidate (protein precipitate of dialyzed ammonium sulfate 0-40%); one group with the purified rCap-PCV-2; one group inoculated with phosphate buffer PBS (negative control); and one group inoculated with commercial vaccines against swine circovirus (positive control). In the groups vaccinated with the vaccinal candidate, with purified protein and the group inoculated with PBS, was added aluminum hydroxide used as adjuvant, except in the animals inoculated with the commercial vaccine. The animals were vaccinated twice (two doses) i.p., with an interval of 14 days between doses. The amount of rCap-PCV-2 inoculated in the vaccinal candidate group and in the group inoculated with purified protein was 30 μg for the first dose and 15 μg for the second. Blood samples were collected via ocular sinus puncture at the 0, 14, 28 and 35 post-vaccination days times to serological analysis. The animals were euthanized 14 days after challenge. All ethical principles for animal experimentation adopted by the Brazilian College of Animal Experimentation (COBEA) were followed (Certificate of Ethics for Animal Use (CEUA)/ UFV, Case No 054/2011).

The evaluation of the humoral immune response was made by indirect ELISA technique. The optimum working concentrations of rCap-PCV-2 antigen and the best dilution of serum (primary antibody) were evaluated by Checker board titration (Crowther J. R. ELISA. Theory and Practice. Methods in Molecular Biology. V. 42, p. 1-223, 1995). It was determined as the optimal antigen (rcap-PCV-2) concentration 0.156 μg/well and 1:4,000, respectively, using for this a positive mouse serum for the PCV-2.

Figure 9:
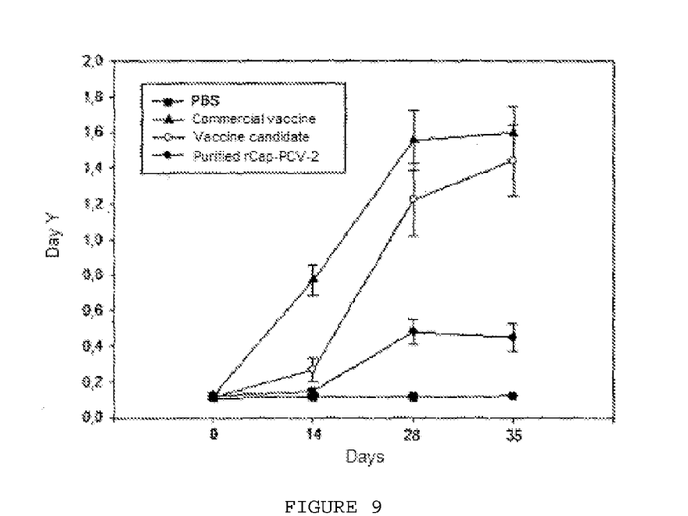

Mice inoculated with the vaccinal candidate showed similar levels to those obtained for mice inoculated with commercial vaccines, especially after the second vaccine dose (FIG. 09), possibly due to the existence of VLPs (FIG. 07), and the adjuvant concentration used.

Experiments in Swine

Swine from a standard commercial farm of twenty-one days old were vaccinated with the candidate vaccinal and compared the commercial vaccines. The antigenic potential of the vaccinal compound containing the recombinant protein of the viral capsid of the PCV-2 (rCap-PCV-2) in swine was evaluated. For this, 140 swine of approximately 21 days old from a commercial farm of Ponte Nova region—MG were used. The experiment was carried out respecting the management adopted by the farm. This field study was conducted following the Standards of Conduct for the use of Animals in Teaching, Research, and Extension from the Department of Veterinary Medicine DVT/UFV, registration number 37/2012.

Figure 11:
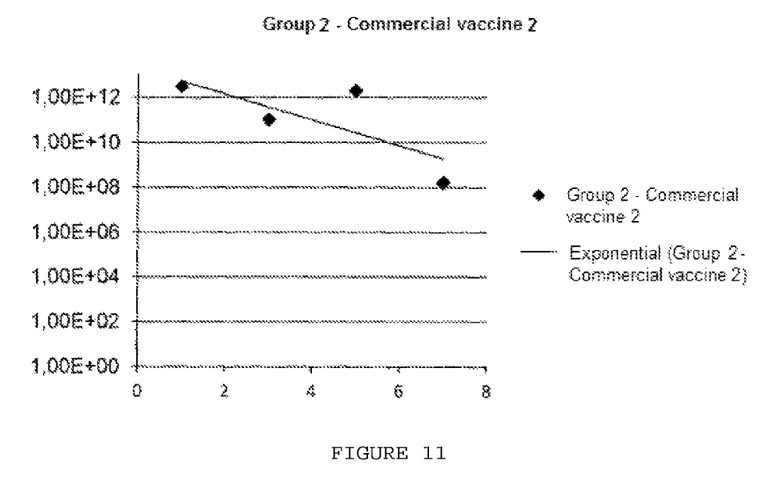
Figure 12:
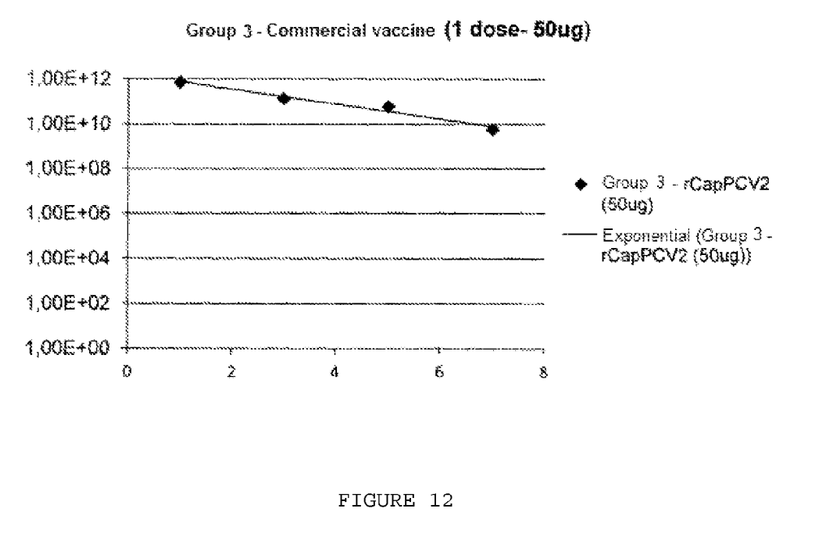
FIG. 12 shows viremia assessment at collection times of the vaccinated animals with the vaccinal candidate with a dose at a concentration of 50 pg. On the vertical axis is shown the viral load, on the horizontal axis is shown the 4 collection steps: 21, 63, 105 and 154 days of swine age. The linear regression is represented by the formula y=2E+12$e^{-0.766x}$. There was a significant decrease in viral load on the period after the vaccination ($R^2$=0.9696).
Figure 13:
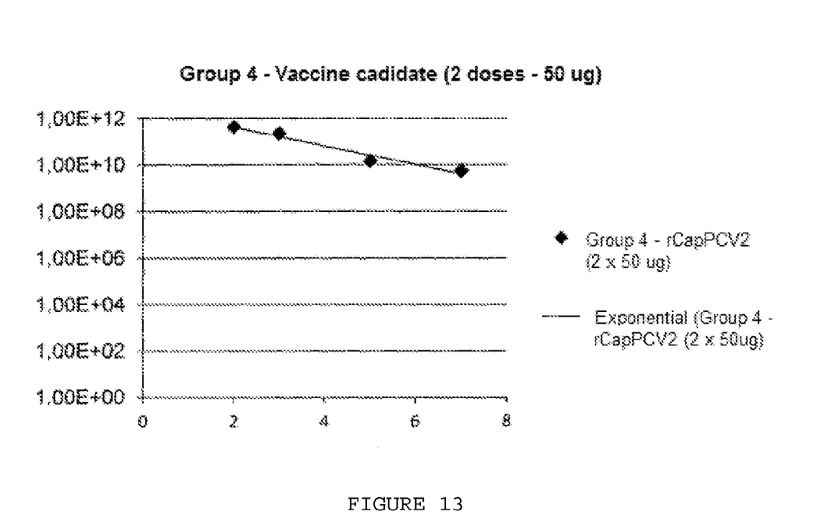
FIG. 13 shows viremia assessment at collection times of the vaccinated animals with the vaccinal candidate with two doses at a concentration of 50 pg. On the vertical axis is shown the viral load, on the horizontal axis is shown the 4 collection steps: 21, 63, 105 and 154 days of swine age. The linear regression is represented by the formula y=1E+12$e^{-0.79x}$. There was a significant decrease in viral load on the period after the vaccination ($R^2$=0.9418).
Figure 14:
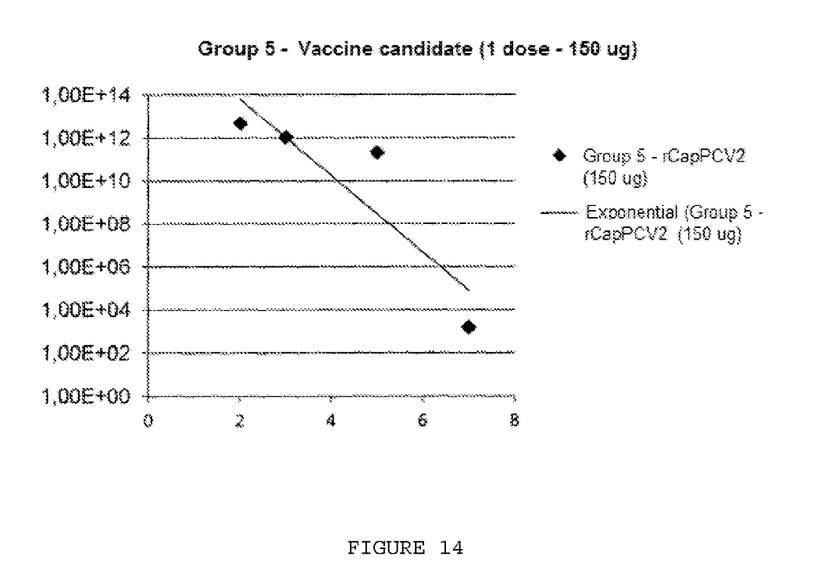
FIG. 14 shows viremia assessment at the collection times of the vaccinated animals with the vaccinal candidate at a dose concentration of 150 µg. On the vertical axis is shown the viral load, on the horizontal axis is shown the 4 collection steps: 21, 63, 105 and 154 days of swine age. The linear regression is represented by the formula y=2E+17$e^{-4.106x}$. There was no significant reduction in viral load on the period after the vaccination ($R^2$=0.7912).
Figure 15:
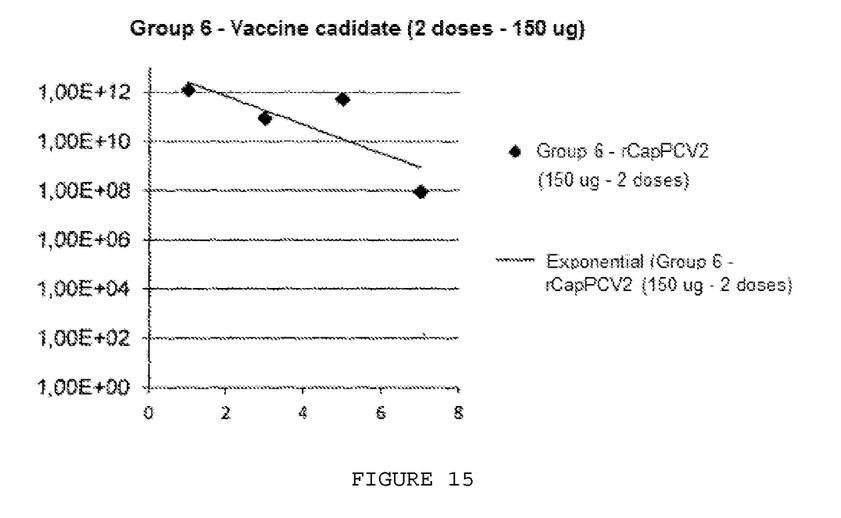
FIG. 15 shows viremia assessment at the collection times of the vaccinated animals with the vaccinal candidate with two doses at a concentration of 150 pg. On the vertical axis is shown the viral load, on the horizontal axis is shown the 4 collection steps: 21, 63, 105 and 154 days of swine age. The linear regression is represented by the formula y=4E+13$e^{-1.594x}$. There was no significant reduction in viral load on the period after the vaccination ($R^2$=0.6673).
Figure 16:
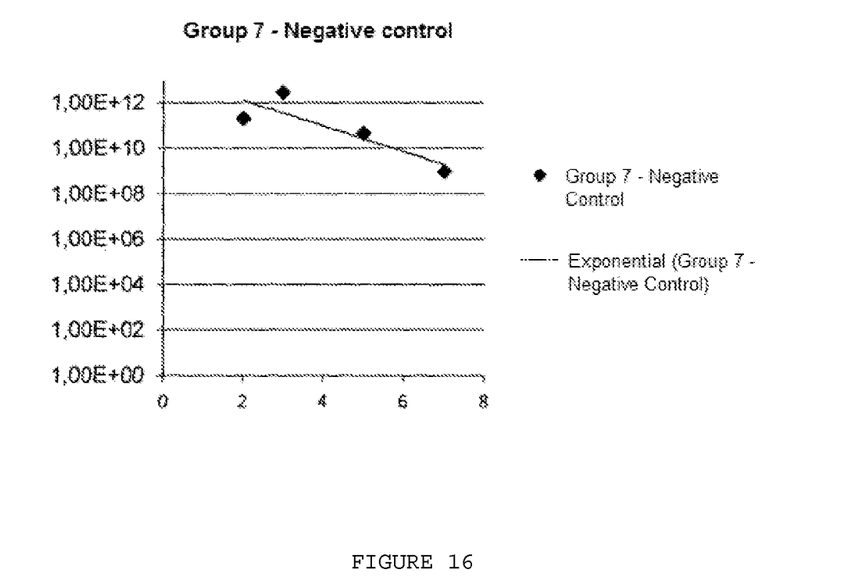

The animals were divided in 7 groups of 20 animals. Groups 1 and 2 were vaccinated with commercial vaccines according to the manufacturer's recommendations. Groups 3 and 4 were vaccinated with the commercial candidate containing 50 μg of the recombinant protein, wherein the animals of group 3 received one dose at 21 days of age and the animals of group 4 received two doses at 21 and 35 days of age. In contrast, 5 and 6 groups were vaccinated with the vaccinal candidate containing 150 μg of the recombinant protein, using one and two doses respectively, in the same vaccinal scheme as groups 3 and 4. The group 7, control group, was vaccinated with phosphate buffer (PBS). All immunizations were performed by intramuscular route. Blood samples were collected from the initial adaptation phase to the day of slaughter for viral load quantification. Blood samples were collected at 21, 63, 105 and 154 life days of the animals. The total DNA extraction was performed using a commercial extraction kit. The quantification of the PCV-2 viral load in the serum collected was performed by PCR in real time according to the protocol described by Silva et al. (Silva, F. M. F., Silva Jr., A., Vidigal P. M., Oliveira C. R., Viana, V. W., Silva, C. H. O., Vargas, I., Fietto, J. L. R., Almeida, M. R. Porcine Circovirus-2 Viral Load versus Lesions in Pigs: Perspectives for Post-weaning multisystemic Wasting Syndrome. Journal of Comparative Pathology, v. 144, p. 296-302, 2011). The reactions were performed in triplicate and all analyzed Ct (threshold cycle) represent the Ct average from each sample, thus, from the Ct average of each sample the averaged and standard deviation per group and collection were calculated. The mean values found were used for the decreasing trend assessment of the viral load through exponential regression analysis. Statically no viral load decreasing trend was observed in commercial vaccines 1 and 2 (FIGS. 10 and 11). A reduction in viral load was statistically demonstrated in groups 3 and 4 (rCap-PCV2 50 pg, one and two doses) $R^2=0.96$ and $R^2=0.94$, respectively (FIGS. 12 and 13), where there was a downward trend from the third week of analysis. Groups 5 and 6 (rCap-PCV2 150 μg—one and two doses) did not show a statically admissible decreasing trend of the viral load ($R^2=0.7184$ and $R^2=0.638$, respectively—FIGS. 14 and 15). The negative control group showed no statistically decreasing trend of the viral load (FIG. 16).

CONCLUSION

Currently, in the veterinary market, the commercial vaccines against PCV-2 are sold by foreign companies, and they are produced outside of Brazil, having thus the cost of imports on the vaccine lots. The vaccine antigens may be used in the vaccination of animals in control programs for PCV-2 associated diseases in the conventional swine production systems and represent alternative to the vaccines commercially available. The ELISA kit may be used in quantification of PCV-2 vaccine antigens, which can be used for quality assurance tests on commercial and/or experimental vaccine.

The invention claimed is:

1. A Porcine Circovirus 2 (PCV-2) recombinant capsid antigen comprising SEQ ID NO: 2.

2. A virus-like particle (VLP) comprising oligomerized recombinant capsid antigen of claim 1.

3. A vaccine composition comprising the recombinant capsid antigen of claim 1 and a pharmaceutically acceptable adjuvant.

4. A capture ELISA diagnostic kit comprising the recombinant capsid antigen of claim 1 and antibodies that bind the recombinant capsid antigen of claim 1.

5. A method of producing a diagnostic kit or vaccine compound comprising the Porcine Circovirus 2 (PCV-2) recombinant capsid antigen of claim 1, comprising providing the Porcine Circovirus 2 (PCV-2) recombinant capsid antigen for the diagnostic kit or vaccine compound.

6. A method of vaccinating swine against PCV-2 comprising administering to the swine an effective amount of the vaccine composition of claim 3.

7. A method of quantifying a capsid protein of PCV-2 comprising performing an ELISA assay with the capture ELISA diagnostic kit of claim 4.

8. A recovery process of the Porcine Circovirus 2 (PCV-2) recombinant capsid antigen of claim 1, comprising:
  a) adding ammonium sulfate $(NH_4)_2SO_4$ to a soluble fraction containing rCap-PCV-2 to a saturation of 20%, followed by sample incubation at 0° C., 100 rpm for 30 minutes;
  b) centrifuging a protein extract at 15,000×g for 20 minutes at 0° C., collecting a supernatant and resuspending a precipitate in a same initial volume as carbonate buffer pH 7.0, containing sodium chloride (NaCl) 300mM;
  c) adding to the supernatant a quantity of ammonium sulfate sufficient to 40% saturation;
  d) repeating steps of incubation and agitation on ice and centrifugation to obtain fractions of 20-40%, 40-60% and 60-80% saturation of ammonium sulfate;
  e) performing dialysis of the fractions in carbonate buffer pH 7.0 containing NaCl 300mM to obtain the Porcine Circovirus 2 (PCV-2) recombinant capsid antigen;
  f) storing the Porcine Circovirus 2 (PCV-2) recombinant capsid antigen.

9. Vaccine Formulations which comprise the VLP as defined in claim 2, further comprising a pharmaceutically acceptable adjuvant.

* * * * *

SEQUENCE LISTING

<160> NUMBER OF SEQ ID NOS: 4

<210> SEQ ID NO 1
<211> LENGTH: 764
<212> TYPE: DNA
<213> ORGANISM: Artificial Sequence
<220> FEATURE:
<223> OTHER INFORMATION: Recombinant Porcine circovirus 2

<400> SEQUENCE: 1
atgggccatc atcatcatca tcatcatcat catcacagca gcggccatat cgaaggtcgt 60
catatgacgt atccaaggag gcgttaccgg agaagaagac accgcccacg cagccatctt 120
ggccagatcc tccgccgccg cccctggctc atccaccccc gccaccgtta ccgctggaga 180
aggaaaaatg gcatcttcaa cacccgcctc tcccgcacct tcggatatac tatcaaacga 240
accacagtca aaacgccctc ctgggcggtg gacatgatga gattcaatat taatgacttt 300
cttcccccag gagggggctc aaacccccgc tctgtgccct ttgaatacta cagaataaga 360
aaggttaagg ttgaattctg gccctgctcc ccgatcaccc agggtgacag gggagtgggc 420
tccagtgctg ttattctaga tgataacttt gtaacaaagg ccacagccct cacctatgac 480
ccctatgtaa actactcctc ccgccatacc ataacccagc ccttctccta ccactcccgc 540
tactttaccc ccaaacctgt cctagattcc actattgatt acttccaacc aaacaacaaa 600
agaaatcagc tgtggctgag actacaaact gctggaaatg tagaccacgt aggcctcggc 660
actgcgttcg aaaacagtat atacgaccag gaatacaata tccgtgtaac catgtatgta 720
caattcagag aatttaatct taaagacccc ccacttaaca ctaa 764

<210> SEQ ID NO 2
<211> LENGTH: 254
<212> TYPE: PRT
<213> ORGANISM: Artificial Sequence
<220> FEATURE:
<223> OTHER INFORMATION: Recombinant Porcine circovirus 2

<400> SEQUENCE: 2

```
Met Gly His His His His His His His His Ser Ser Gly His
1               5                   10                  15

Ile Glu Gly Arg His Met Thr Tyr Pro Arg Arg Arg Tyr Arg Arg Arg
            20                  25                  30

Arg His Arg Pro Arg Ser His Leu Gly Gln Ile Leu Arg Arg Arg Pro
        35                  40                  45

Trp Leu Ile His Pro Arg His Arg Tyr Arg Trp Arg Arg Lys Asn Gly
    50                  55                  60

Ile Phe Asn Thr Arg Leu Ser Arg Thr Phe Gly Tyr Thr Ile Lys Arg
65                  70                  75                  80

Thr Thr Val Lys Thr Pro Ser Trp Ala Val Asp Met Met Arg Phe Asn
                85                  90                  95

Ile Asn Asp Phe Leu Pro Pro Gly Gly Gly Ser Asn Pro Arg Ser Val
            100                 105                 110

Pro Phe Glu Tyr Tyr Arg Ile Arg Lys Val Lys Val Glu Phe Trp Pro
        115                 120                 125

Cys Ser Pro Ile Thr Gln Gly Asp Arg Gly Val Gly Ser Ser Ala Val
    130                 135                 140

Ile Leu Asp Asp Asn Phe Val Thr Lys Ala Thr Ala Leu Thr Tyr Asp
145                 150                 155                 160

Pro Tyr Val Asn Tyr Ser Ser Arg His Thr Ile Thr Gln Pro Phe Ser
                165                 170                 175

Tyr His Ser Arg Tyr Phe Thr Pro Lys Pro Val Leu Asp Ser Thr Ile
            180                 185                 190

Asp Tyr Phe Gln Pro Asn Asn Lys Arg Asn Gln Leu Trp Leu Arg Leu
        195                 200                 205

Gln Thr Ala Gly Asn Val Asp His Val Gly Leu Gly Thr Ala Phe Glu
    210                 215                 220

Asn Ser Ile Tyr Asp Gln Glu Tyr Asn Ile Arg Val Thr Met Tyr Val
225                 230                 235                 240

Gln Phe Arg Glu Phe Asn Leu Lys Asp Pro Pro Leu Asn Thr
                245                 250
```

<210> SEQ ID NO 3
<211> LENGTH: 702
<212> TYPE: DNA
<213> ORGANISM: Porcine circovirus 2

<400> SEQUENCE: 3

```
atgacgtatc caaggaggcg ttaccggaga agaagacacc gcccacgcag ccatcttggc     60
cagatcctcc gccgccgccc ctggctcatc cacccccgcc accgttaccg ctggagaagg    120
aaaaatggca tcttcaacac ccgcctctcc cgcaccttcg gatatactat caaacgaacc    180
acagtcaaaa cgccctcctg ggcggtggac atgatgagat tcaatattaa tgactttctt    240
cccccaggag gggctcaaa cccccgctct gtgccctttg aatactacag aataagaaag    300
gttaaggttg aattctggcc ctgctccccg atcacccagg gtgacagggg agtgggctcc    360
agtgctgtta ttctagatga taactttgta acaaaggcca cagccctcac ctatgacccc    420
```

```
tatgtaaact actcctcccg ccataccata acccagccct tctcctacca ctcccgctac    480
tttaccccca aacctgtcct agattccact attgattact tccaaccaaa caacaaaaga    540
aatcagctgt ggctgagact acaaactgct ggaaatgtag accacgtagg cctcggcact    600
gcgttcgaaa acagtatata cgaccaggaa tacaatatcc gtgtaaccat gtatgtacaa    660
ttcagagaat taatcttaa agacccccca cttaacactt aa                      702
```

<210> SEQ ID NO 4
<211> LENGTH: 233
<212> TYPE: PRT
<213> ORGANISM: Porcine circovirus 2

<400> SEQUENCE: 4

```
Met Thr Tyr Pro Arg Arg Tyr Arg Arg Arg Arg His Arg Pro Arg
1               5                   10                  15

Ser His Leu Gly Gln Ile Leu Arg Arg Arg Pro Trp Leu Ile His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Ile Lys Arg Thr Thr Val Lys Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Thr
225                 230
```